(12) United States Patent
Katsuki

(10) Patent No.: US 11,265,450 B2
(45) Date of Patent: Mar. 1, 2022

(54) IMAGING SYSTEM AND CONTROL DEVICE FOR DETERMINING HIGH-LUMINANCE REGION AND REDUCTION LIGHT AMOUNT TO ILLUMINATE REGION

(71) Applicant: Sony Corporation, Tokyo (JP)

(72) Inventor: Shinji Katsuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/256,652

(22) PCT Filed: Jul. 25, 2019

(86) PCT No.: PCT/JP2019/029180
§ 371 (c)(1),
(2) Date: Dec. 29, 2020

(87) PCT Pub. No.: WO2020/031717
PCT Pub. Date: Feb. 13, 2020

(65) Prior Publication Data
US 2021/0266435 A1  Aug. 26, 2021

(30) Foreign Application Priority Data

Aug. 7, 2018 (JP) .............................. JP2018-148505

(51) Int. Cl.
*H04N 5/225* (2006.01)
*H04N 5/235* (2006.01)

(52) U.S. Cl.
CPC ......... *H04N 5/2256* (2013.01); *H04N 5/2352* (2013.01)

(58) Field of Classification Search
CPC .... H04N 5/2256; H04N 5/2352; H04N 5/225; H04N 5/243; H04N 5/235; A61B 1/045;
(Continued)

(56) References Cited

U.S. PATENT DOCUMENTS

2005/0178950 A1  8/2005  Yoshida

FOREIGN PATENT DOCUMENTS

JP   2005-236513 A   9/2005
JP   2010-237253 A   10/2010
(Continued)

OTHER PUBLICATIONS

Translation of JP 2010-237253 (Year: 2010).*
(Continued)

*Primary Examiner* — Twyler L Haskins
*Assistant Examiner* — Angel L Garces-Rivera
(74) *Attorney, Agent, or Firm* — Xsensus LLP

(57) ABSTRACT

An imaging system includes an imaging device that images a predetermined imaging area, an illumination device that performs irradiation with illumination light so as to illuminate an imaging area and is capable of adjusting a light amount of the illumination light for each of local regions narrower than the imaging area, and a control unit that controls the imaging device and the illumination device. Then, a high-luminance region having a luminance value exceeding a predetermined luminance range is detected in an image captured by the imaging device, and a light amount of illumination light with which the illumination device irradiates a local region corresponding to the high-luminance region is determined to be a reduction light amount reduced to be less than a light amount with respect to overall of the imaging area. The present technology can be applied to, for example, a camera system for operation.

11 Claims, 10 Drawing Sheets

(58) Field of Classification Search
CPC .......... A61B 1/06; G03B 7/091; G03B 15/14; G03B 15/05
See application file for complete search history.

(56) References Cited

FOREIGN PATENT DOCUMENTS

| JP | 2013-118429 A | 6/2013 |
| WO | 2016/104386 A1 | 6/2016 |

OTHER PUBLICATIONS

International Search Report and Written Opinion dated Sep. 17, 2019, received for PCT Application No. PCT/JP2019/029180, Filed on Jul. 25, 2019, 9 pages including English Translation.

\* cited by examiner

FIG. 2
SDR IMAGE
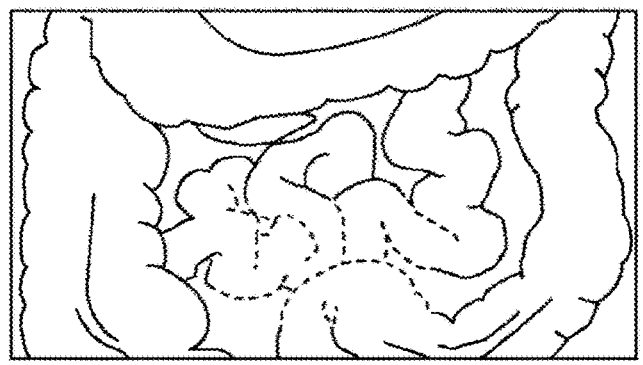
LOCAL ILLUMINATION HDR IMAGE
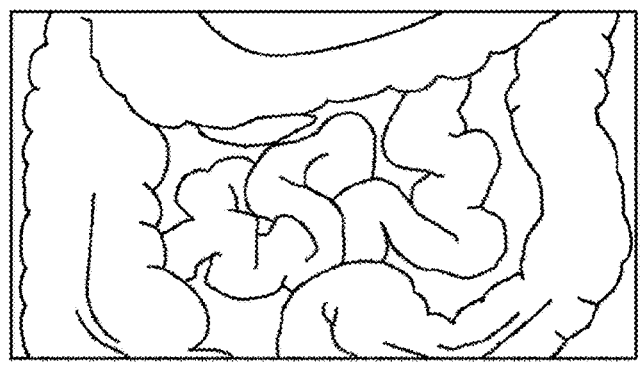

IMAGING SYSTEM AND CONTROL DEVICE FOR DETERMINING HIGH-LUMINANCE REGION AND REDUCTION LIGHT AMOUNT TO ILLUMINATE REGION

CROSS-REFERENCE TO RELATED APPLICATIONS

The present application is based on PCT filing PCT/JP2019/029180, filed Jul. 25, 2019, which claims priority to JP 2018-148505, filed Aug. 7, 2018, the entire contents of each are incorporated herein by reference.

TECHNICAL FIELD

The present disclosure relates to an imaging system, a control device, and a control method, and more particularly to an imaging system, a control device, and a control method that enable acquisition of an image in which an operative field is better visible.

BACKGROUND ART

Conventionally, in an operation using an observation system for operation utilizing an endoscope, a video microscope, an open imaging operative field camera, or the like, a surgeon visually recognizes an affected area with an image acquired by imaging an operative field including an organ, or the like, of a patient. By the way, depending on an organ to be operated on, there are both a region in which incident light is diffusely reflected in various directions and a region in which incident light is specularly reflected in one direction due to adhesion of water, oil, or the like. Therefore, an operative field imaged by an observation system for operation has often been a subject with a very wide dynamic range.

With this arrangement, with an operation using an observation system for operation, there is a concern that overexposure, underexposure, or the like may occur in a standard dynamic range (SDR) image captured in a standard dynamic range depending on a condition of exposure on an organ. Thus, it is expected that a surgeon has difficulty in well visually recognizing a condition of an operative field. Therefore, there has been a need for an observation system for operation that can acquire a high dynamic range (HDR) image that is captured in a wider dynamic range than an SDR image is.

For example, Patent Document 1 discloses an imaging system that sets an exposure amount for generating an exposure amount for an HDR image according to a timing of exposure processing on the basis of a reference exposure amount calculated from a detection result of detecting brightness of the image.

CITATION LIST

Patent Document

Patent Document 1: WO 2016/104386

SUMMARY OF THE INVENTION

Problems to be Solved by the Invention

However, in a conventional imaging system, in order to capture an HDR image, for example, there has been need for a configuration uses a very large sized image sensor as compared with an image sensor having a normal dynamic range. Therefore, there is demand for an imaging system capable of capturing an image in which an operative field is better visible even with a configuration using an image sensor having a normal dynamic range.

The present disclosure has been made to solve the problems mentioned above, and an object of the present disclosure is to enable acquiring an image in which an operative field is better visible.

Solutions to Problems

An imaging system according to one aspect of the present disclosure includes
an imaging device that images a predetermined imaging area, an illumination device that performs irradiation with illumination light so as to illuminate the imaging area and is capable of adjusting a light amount of the illumination light for each of local regions narrower than the imaging area, and a control unit that controls the imaging device and the illumination device, in which the control unit has a detection unit that detects a high-luminance region having a luminance value exceeding a predetermined luminance range in an image captured by the imaging device, and has a light amount determination unit that determines a light amount of the illumination light with which the illumination device irradiates the local region corresponding to the high-luminance region to be a reduction light amount reduced to be less than a light amount with respect to overall of the imaging area.

A control device according to one aspect of the present disclosure controls an imaging device that images a predetermined imaging area and an illumination device that performs irradiation with illumination light so as to illuminate the imaging area and is capable of adjusting a light amount of the illumination light for each of local regions narrower than the imaging area, and includes a detection unit that detects a high-luminance region having a luminance value exceeding a predetermined luminance range in an image captured by the imaging device, and a light amount determination unit that determines a light amount of the illumination light with which the illumination device irradiates the local region corresponding to the high-luminance region to be a reduction light amount reduced to be less than a light amount with respect to overall of the imaging area.

A control method according to one aspect of the present disclosure includes, by a control device that controls an imaging device that images a predetermined imaging area and an illumination device that performs irradiation with illumination light so as to illuminate the imaging area and is capable of adjusting a light amount of the illumination light for each of local regions narrower than the imaging area, detecting a high-luminance region having a luminance value exceeding a predetermined luminance range in an image captured by the imaging device, and determining a light amount of the illumination light with which the illumination device irradiates the local region corresponding to the high-luminance region to be a reduction light amount reduced to be less than a light amount with respect to overall of the imaging area.

In one aspect of the present disclosure, control is performed on an imaging device that images a predetermined imaging area, and an illumination device that performs irradiation with illumination light so as to illuminate an imaging area and is capable of adjusting a light amount of the illumination light for each of local regions narrower than the imaging area. Then, a high-luminance region having a luminance value exceeding a predetermined luminance range is detected in an image captured by the imaging device, and a light amount of illumination light with which the illumination device irradiates a local region corresponding to the high-luminance region is determined to be a reduction light amount reduced to be less than a light amount with respect to overall of the imaging area.

Effects of the Invention

According to one aspect of the present disclosure, it is possible to acquire an image in which an operative field is better visible.

Note that the effects described here are not necessarily limited, and may be any one of the effects described in the present disclosure.

BRIEF DESCRIPTION OF DRAWINGS

FIG. 2 is a diagram for describing an SDR image and a local illumination HDR image in comparison.

MODE FOR CARRYING OUT THE INVENTION

Hereinafter, a specific embodiment to which the present technology is applied will be described in detail with reference to the drawings.

<Configuration Example of Camera System for Operation>

A situation in which a camera system for operation to which the present technology is applied is utilized will be described with reference to FIG. 1.

Figure 1:
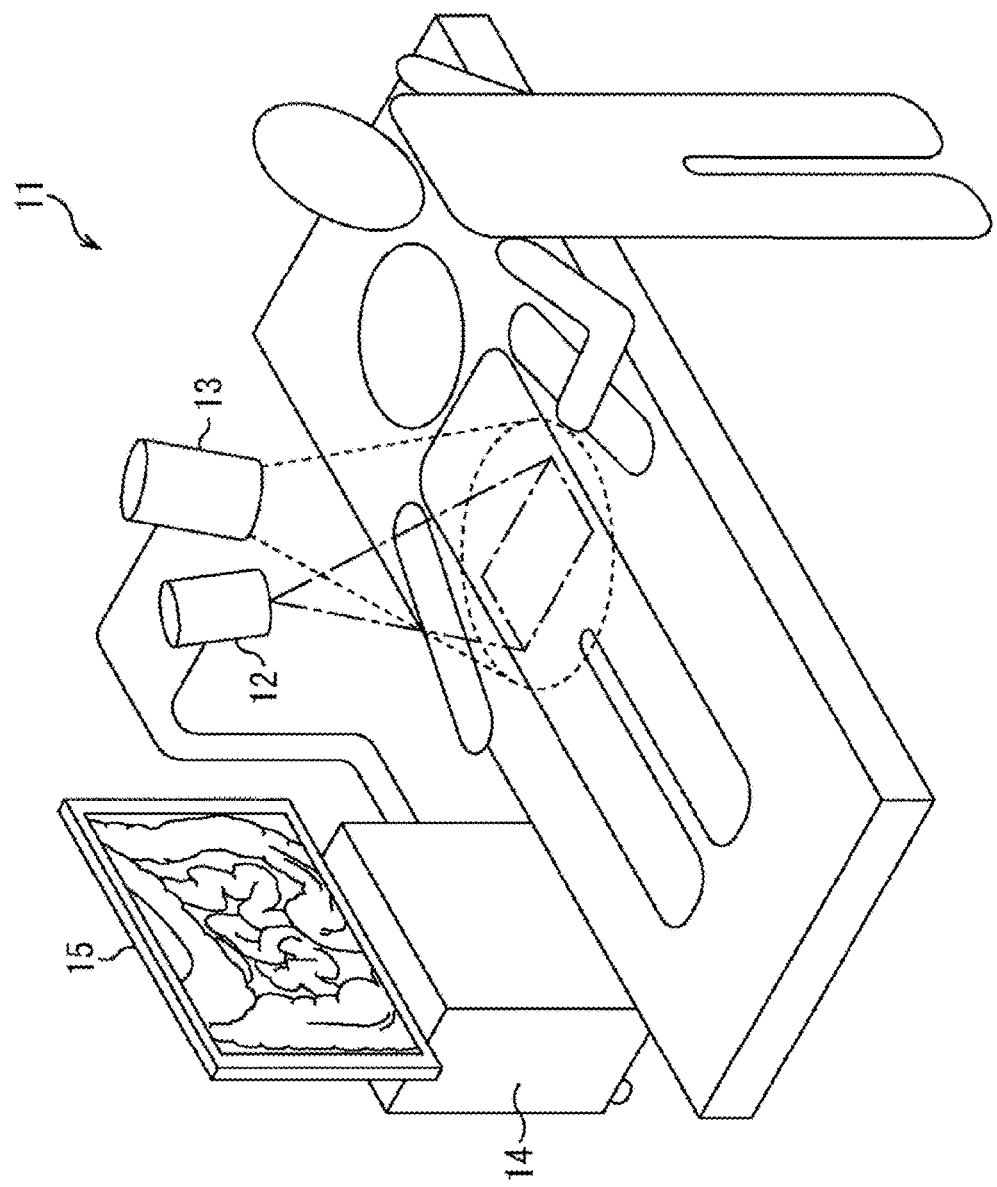
FIG. 1 is a block diagram illustrating a configuration example of an embodiment of a camera system for operation to which the present technology is applied.

A camera system for operation 11 illustrated in FIG. 1 is utilized, for example, when a surgeon performs an operation on a patient on a patient bed, and configured including an imaging device 12, an illumination device 13, a controller 14, and a display device 15. Furthermore, the camera system for operation 11 is considered to be utilized for an endoscope, a video microscope, an open imaging operative field camera, or the like.

For example, in the camera system for operation 11, the imaging device 12 and the illumination device 13 are mounted on a support arm (not illustrated) so that a positional relation with each other is fixed, and are supported in any position and orientation according to operation by a surgeon. Furthermore, the support arm on which the imaging device 12 and the illumination device 13 are mounted is fixed to the controller 14, and the imaging device 12, the illumination device 13, and the controller 14 are connected via a communication cable, an optical fiber, or the like.

The imaging device 12 is configured including an image sensor such as a complementary metal oxide semiconductor (CMOS) image sensor, and images an imaging area (for example, a region surrounded by an alternate long and short dash line in FIG. 1) including, in an operative field, an affected area of a patient on whom the surgeon performs operation. For example, in a configuration in which the camera system for operation 11 is utilized as an endoscope, a scope, which is not illustrated, is connected to the imaging device 12, and the imaging device 12 can capture an image of an affected area through the scope. Then, data output from the image sensor of the imaging device 12 is provided to the controller 14 and used as an image signal. Note that the image sensor included in the imaging device 12 is not configured large with a wide dynamic range, but is configured small for imaging in a normal dynamic range.

The illumination device 13 irradiates the affected area with illumination light so as to illuminate the imaging area of the imaging device 12. Then, the illumination device 13 is configured so that a light amount of illumination light can be adjusted for each region (hereinafter, referred to as a local region) of a plurality of regions, which is narrower than the imaging area and is divided, by the imaging device 12, from an area which can be irradiated with illumination light (for example, a region surrounded by a dashed line in FIG. 1). For example, as the illumination device 13, a projection type image display device such as a projector can be utilized.

The controller 14 performs various controls of the imaging device 12 and the illumination device 13 on the basis of an image captured by the imaging device 12, performs image processing on the image, and provides the image to the display device 15. For example, the controller 14 can perform automatic exposure (AE) control including control of an electronic shutter, aperture, gain, or the like, of the imaging device 12.

Moreover, the controller 14 detects a high-luminance region having a luminance value exceeding a predetermined luminance range in the image, and perform control for adjusting a light amount so that a light amount of illumination light that irradiates a local region corresponding to the high-luminance region to be reduced to be less than a light amount with respect to overall of the imaging area. Then, the controller 14 performs image processing for amplifying a luminance value of the image in the local region in which a light amount is reduced, according to the reduced light amount. Hereinafter, such control for adjusting a light amount for each local region and image processing for amplifying a luminance value according to a reduced light amount are referred to as local illumination light control processing. Furthermore, a detailed configuration of the controller 14 will be described later with reference to FIG. 4.

The display device 15 displays an image acquired by being subjected to local illumination light control processing in the controller 14, the image having a wide dynamic range in which an overall screen is controlled to proper brightness (hereinafter, referred to as a local illumination HDR image as appropriate). That is, a local illumination HDR image is an image in which a light amount of illumination light that irradiates a local region corresponding to a high-luminance region is reduced, and a luminance value in the local region is amplified according to the reduced light amount. Here, the display device 15 uses a so-called HDR monitor that supports display of an HDR image (for example, luminance of the image can be reproduced with 12 bits or more).

The camera system for operation 11 is configured in this way, and a local illumination HDR image in which occurrence of overexposure, or the like, is avoided, can be acquired by using an imaging device 12 including a small image sensor that captures an image with a normal dynamic range. Therefore, when performing an operation by utilizing the camera system for operation 11, the surgeon can better visually recognize an operative field with a local illumination HDR image displayed on the display device 15.

For example, as described above, in an organ to be operated on, there are both a region in which light is diffusely reflected and a region in which light is specularly reflected. Therefore, in a part where reflected light reflects very strongly due to adhesion of water, oil, or the like in an SDR image, saturation occurs in which electric charge photoelectrically converted by a pixel of an image sensor is saturated and overflows, and overexposure occurs as a result of performing AE control.

That is, as in the SDR image illustrated in FIG. 2, if an image of a part with strong reflected light that specularly reflects light is captured, the part becomes a high-luminance region (the region drawn by a dashed line) in which overexposure occurs.

Meanwhile, the camera system for operation 11 can avoid occurrence of saturation in the image sensor included in the imaging device 12 by reducing a light amount of illumination light that irradiates a local region corresponding to the high-luminance region. Moreover, by performing image processing to amplify a luminance value of a local region where a light amount of illumination light is reduced according to the reduced light amount, for example, by multiplying an image signal by a reciprocal of the amount, the camera system for operation 11 can restore brightness of the local region.

Furthermore, the camera system for operation 11 uses so-called an HDR signal, such as Hybrid Log-Gamma (HLG) or Perceptual Quantization (PQ) as an image signal on which local illumination light control processing is performed. With this arrangement, the camera system for operation 11 can display a saturation-free local illumination HDR image with a wide dynamic range on the display device 15.

That is, as in a local illumination HDR image illustrated in FIG. 2, saturation does not occur in a high-luminance region where overexposure has occurred in an SDR image, and reproduction with an appropriate tone is possible on the display device 15 in which an HDR monitor is used.

Figure 3:
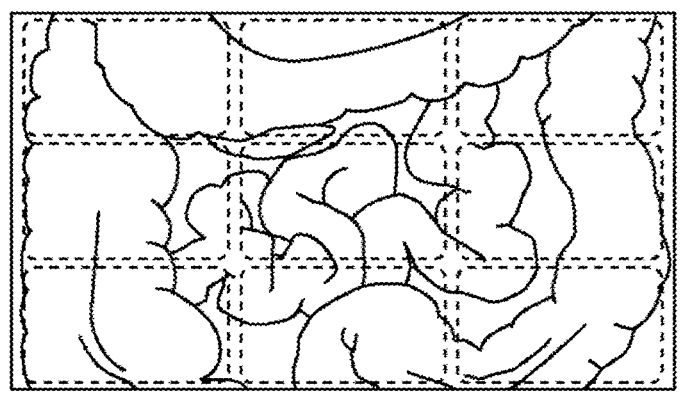
FIG. 3 is a diagram illustrating an example of a local region.

Furthermore, FIG. 3 illustrates an example in which an imaging region is divided into nine 3×3 local regions. In the camera system for operation 11, the illumination device 13 can adjust a light amount of illumination light for each such local region.

Note that an imaging area is not limited to the example illustrated in FIG. 3 but only required to be divided into a plurality of local regions so as to be narrower than an imaging area of the imaging device 12, and the imaging area may be divided by more fine local regions (ultimately, in units of pixels). Furthermore, a shape of a local region can also be various, and, for example, can be deformed according to a shape of a high-luminance region.

For example, in the illumination device 13, as a method for controlling a light amount of illumination light for each local region, there is considered using a method for projecting an image that darkens corresponding to a local region of which a light amount is reduced by utilizing a projector, a method for controlling a light amount for each local region by utilizing local dimming used for backlight control of a liquid crystal panel, or the like. By adopting such a configuration, it is possible to control brightness in units of pixels in a projector or local dimming.

Here, reflection of a subject in an operative image will be described.

For example, when a certain light source illuminates an ideal uniform diffuse reflection surface, illuminance E [lx] of the reflection surface and luminance L [cd/m$^2$] of the reflection surface have a relation as presented by the following mathematical formula (1) by using reflectance ρ.

[Mathematical Formula 1]

$$L = \frac{\rho}{\pi} \times E \tag{1}$$

Meanwhile, when a certain light source illuminates a specular reflection surface (for example, a mirror surface), luminance L [cd/m$^2$] of the specular reflection surface is proportional to luminance of the light source, not illuminance, and is obtained as represented by the following mathematical formula (2) by using the luminance Ls [cd/m$^2$] and reflectance a of the light source.

[Mathematical Formula 2]

$$L = \alpha \times Ls \tag{2}$$

Generally, depending on a shape or a material direction of a reflection surface, the reflection surface include a specularly reflected part and a diffusely reflected (actually, angle dependent not uniformly reflected but ununiformly) part. Thus, in a medical equipment system including a camera, a subject (object) includes a part shadowed from a light source, a diffusely reflected part that depends on illuminance, and a specularly reflected part caused by water, oil, or the like, which depends on luminance of the light source. In a diffusely reflected part, even if reflectance changes from 10% to 90%, which means a change of 10% to 90%, reflective luminance changes depending on a distance. Meanwhile, because the specularly reflected part is proportional to luminance, not illuminance, in a case of a 100% specularly reflective surface, for example, luminance of the light source has reflective luminance of 100% independent of a distance to a subject.

Therefore, a subject including the both has a wide luminance dynamic range, and overexposure occurs in an SDR image as described with reference to FIG. 2. Meanwhile, in the camera system for operation 11, even with a subject including the both, a local illumination HDR image in which occurrence of overexposure is avoided can be acquired.

Furthermore, in the camera system for operation 11, the imaging device 12 can have a compact configuration for capturing an image in a normal dynamic range, can be installed in a small space, and can further reduce cost.

<Configuration Example of Controller>

Figure 4:
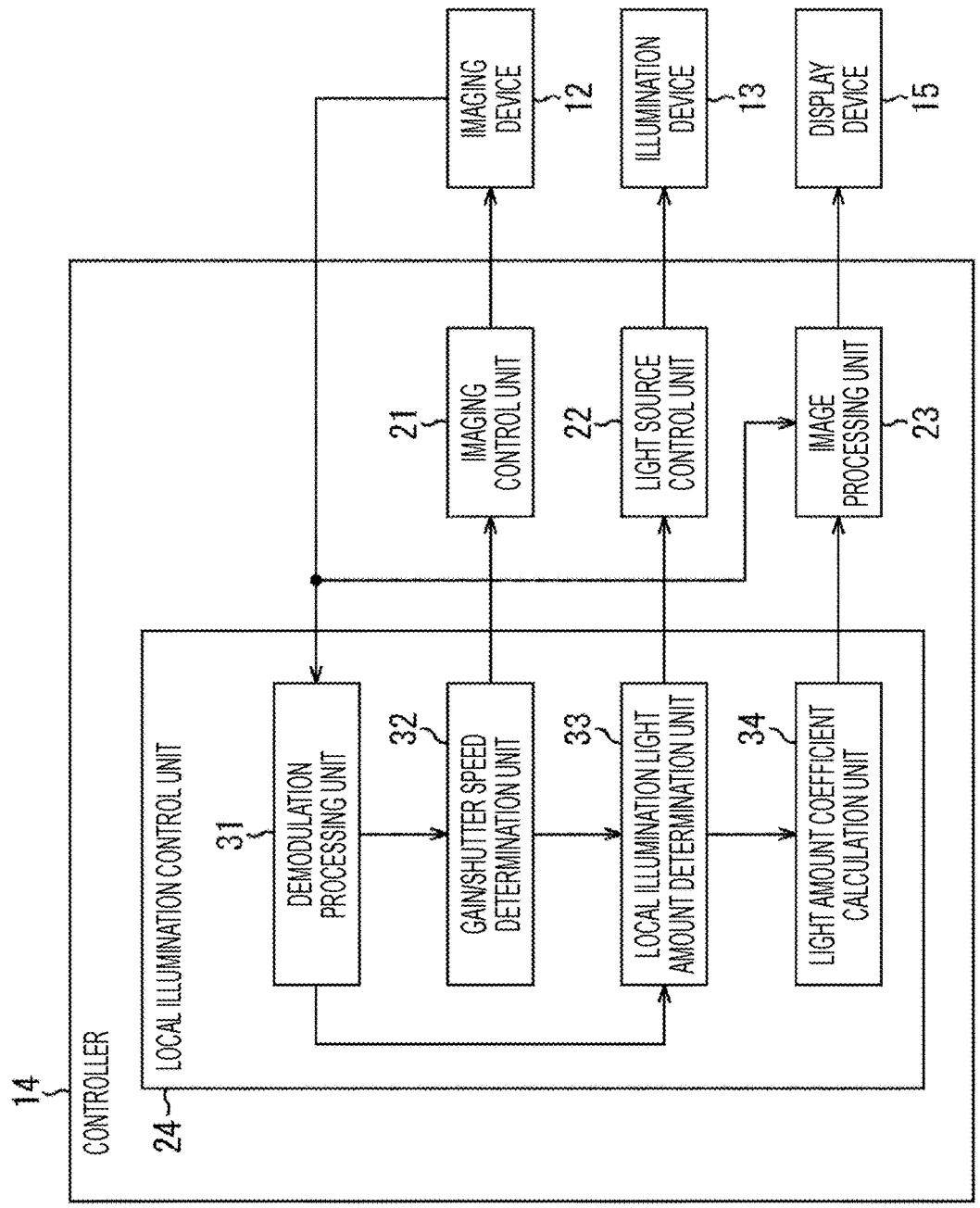
FIG. 4 is a block diagram illustrating a configuration example of an embodiment of a controller.

FIG. 4 is a block diagram illustrating a configuration example of an embodiment of the controller 14.

As described with reference to FIG. 1, the imaging device 12, the illumination device 13, and the display device 15 are connected to the controller 14. Then, the controller 14 is configured including an imaging control unit 21, a light source control unit 22, an image processing unit 23, and a local illumination control unit 24. Furthermore, the local illumination control unit 24 has a demodulation processing unit 31, a gain/shutter speed determination unit 32, a local illumination light amount determination unit 33, and a light amount coefficient calculation unit 34.

The imaging control unit 21 performs various controls of imaging performed by the imaging device 12. For example, the imaging control unit 21 can control the imaging device 12 so as to capture an image at a gain and shutter speed determined by the gain/shutter speed determination unit 32, as well as control switching of zoom magnification, an optical filter, or the like.

The light source control unit 22 performs various controls of light with which the illumination device 13 perform irradiation. For example, the light source control unit 22 can control the illumination device 13 so that irradiation with illumination light is performed for each local region with a light amount determined by the local illumination control unit 24, as well as control on/off, an irradiation timing, or the like, of the illumination light.

The image processing unit 23 performs various image processing on an image captured by the imaging device 12. For example, the image processing unit 23 performs image processing to amplify a luminance value in a local region where a light amount is reduced, according to a light amount coefficient calculated by the light amount coefficient calculation unit 34, as well as performs image processing such as gamma correction or white balance adjustment.

For example, the local illumination control unit 24 previously holds information for which a local region with respect to an imaging region is specified on the basis of an image, which is captured by the imaging device 12, of a state where illumination light is turned on for each local region that the illumination device 13 can separately irradiate with illumination light. That is, it is assumed that the local illumination control unit 24 recognizes a correspondence between an image and a local region.

The image captured by the imaging device 12 is provided to the demodulation processing unit 31. Then, the demodulation processing unit 31 obtains luminance information of an overall screen by performing demodulation over the overall screen with respect to the image, and provides the luminance information to the gain/shutter speed determination unit 32. Furthermore, the demodulation processing unit 31 obtains luminance information of each local region by performing demodulation (for example, simple integration, peak demodulation, a combination thereof, or the like) independently for each local region with respect to the image, and provides the luminance information to the local illumination light amount determination unit 33.

The gain/shutter speed determination unit 32 determines a gain and shutter speed at which the imaging device 12 can image with appropriate exposure over the overall screen according to the luminance information of the overall screen, which is provided from the demodulation processing unit 31.

Figure 5:
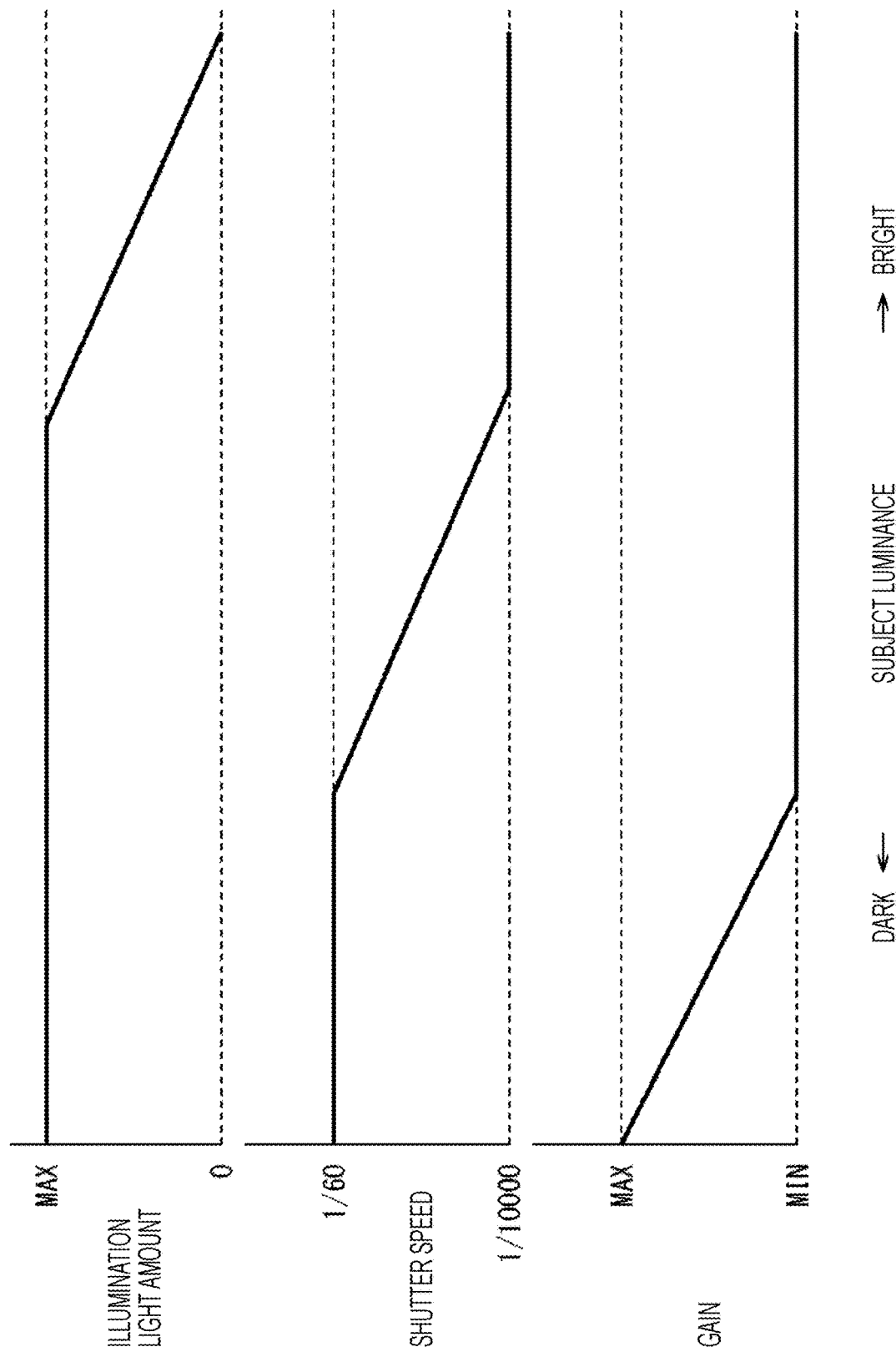
FIG. 5 is a general program diagram used to determine a light amount of illumination light.

For example, the gain/shutter speed determination unit 32 can determine a gain and the shutter speed according to subject luminance of an overall image with reference to a program diagram as illustrated in FIG. 5. Then, the gain/shutter speed determination unit 32 notifies the local illumination light amount determination unit 33 of the gain and the shutter speed, while instructing the imaging control unit 21. With this arrangement, the imaging control unit 21 controls the imaging device 12 so as to capture an image at the gain and shutter speed.

The local illumination light amount determination unit 33 determines a light amount of illumination light for each local region on the basis of the gain and shutter speed provided from the gain/shutter speed determination unit 32 and luminance information for each local region provided from the demodulation processing unit 31.

For example, the local illumination light amount determination unit 33 first determines a maximum light amount allowed for the overall screen from the gain and shutter speed, as will be described later with reference to FIGS. 6 and 7. Note that in a case where local illumination light control processing is not performed, an overall irradiation region of the illumination light is irradiated with illumination light of this light amount, which is hereinafter referred to as an overall light amount.

Then, after detecting a high-luminance region according to luminance information for each local region, the local illumination light amount determination unit 33 reduces a light amount from the overall light amount to a light amount with which occurrence of saturation in a high-luminance region is avoided, and determines a light amount of the illumination light that irradiates the local region (hereinafter, referred to as a local illumination light amount). Then, the local illumination light amount determination unit 33 notifies the light amount coefficient calculation unit 34 of the overall light amount and the local illumination light amount, while instructing the local illumination control unit 24. With this arrangement, the imaging control unit 21 controls the illumination device 13 so as to perform irradiation with illumination light with the overall light amount and local illumination light amount.

The light amount coefficient calculation unit 34 determines, on the basis of the overall light amount and local illumination light amount provided from the local illumination light amount determination unit 33, a light amount coefficient used by the image processing unit 23 to perform image processing, and notifies the image processing unit 23 of the light amount coefficient. For example, a reciprocal of a ratio of a local illumination light amount to an overall light amount is used for a light amount coefficient. To describe an example, in a case where a ratio of a local illumination light amount to an overall light amount is ½, a light amount coefficient is 2.

<Method for Determining Light Amount of Illumination Light>

A determination method for determining a light amount of illumination light for each local region by the local illumination light amount determination unit 33 will be described with reference to FIGS. 5 to 7.

FIG. 5 illustrates a general program diagram used to determine a light amount of illumination light.

In general AE control, an image signal is demodulated by integration of an entire screen or integration by putting weight on a center as a demodulation frame, and illumination intensity, shutter speed, and a gain are controlled so that a target value in the demodulation has an optimal exposure value. The program diagram illustrated in FIG. 5 is formed to reflect demand for keeping a gain as low as possible from a viewpoint of a signal-to-noise ratio (SN ratio) and to have shutter speed as high as possible from a viewpoint of a blur that appears on an image.

Figure 6:
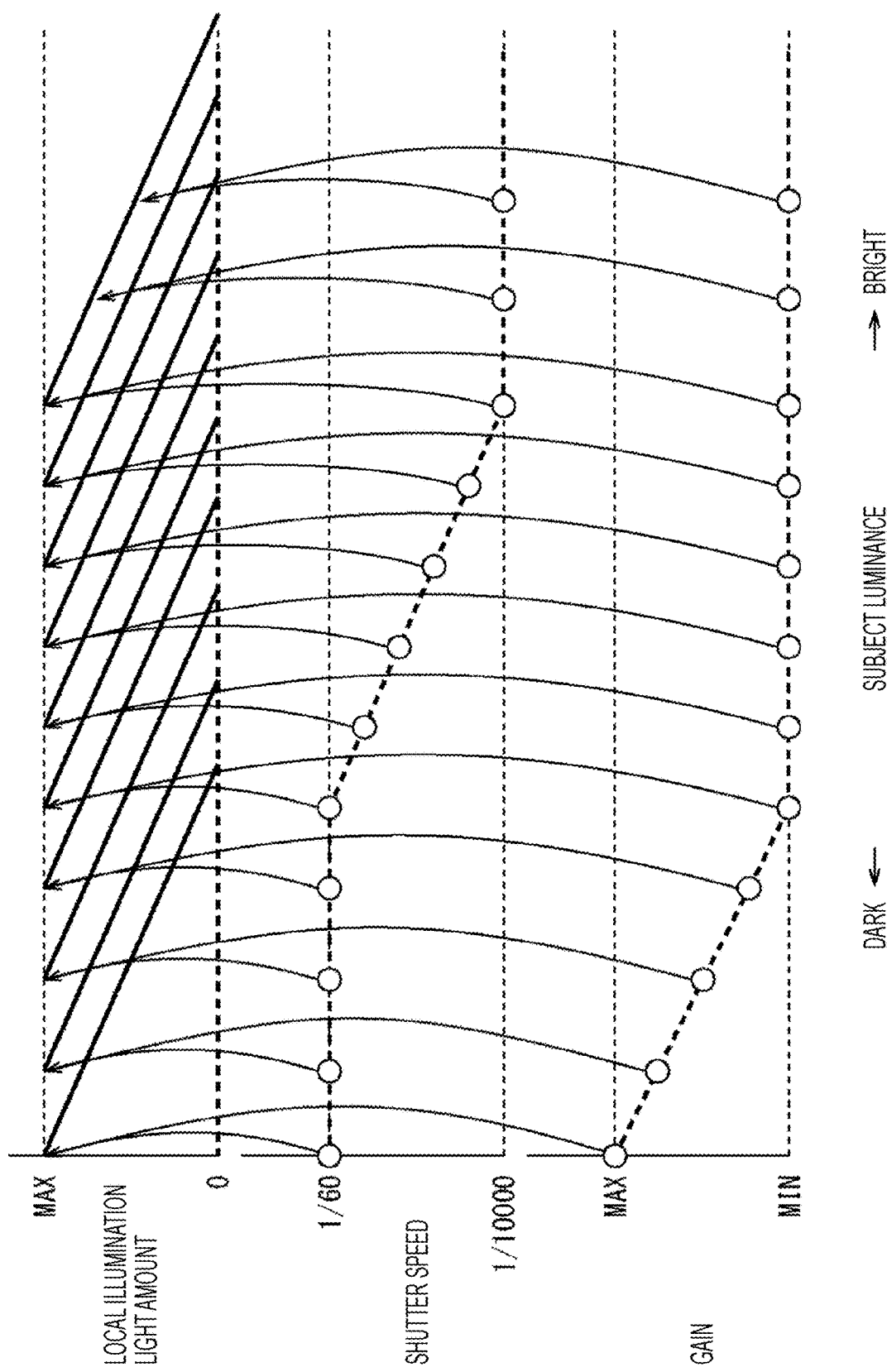
FIG. 6 is a general program diagram used to determine a light amount of illumination light for each local region.
Figure 7:
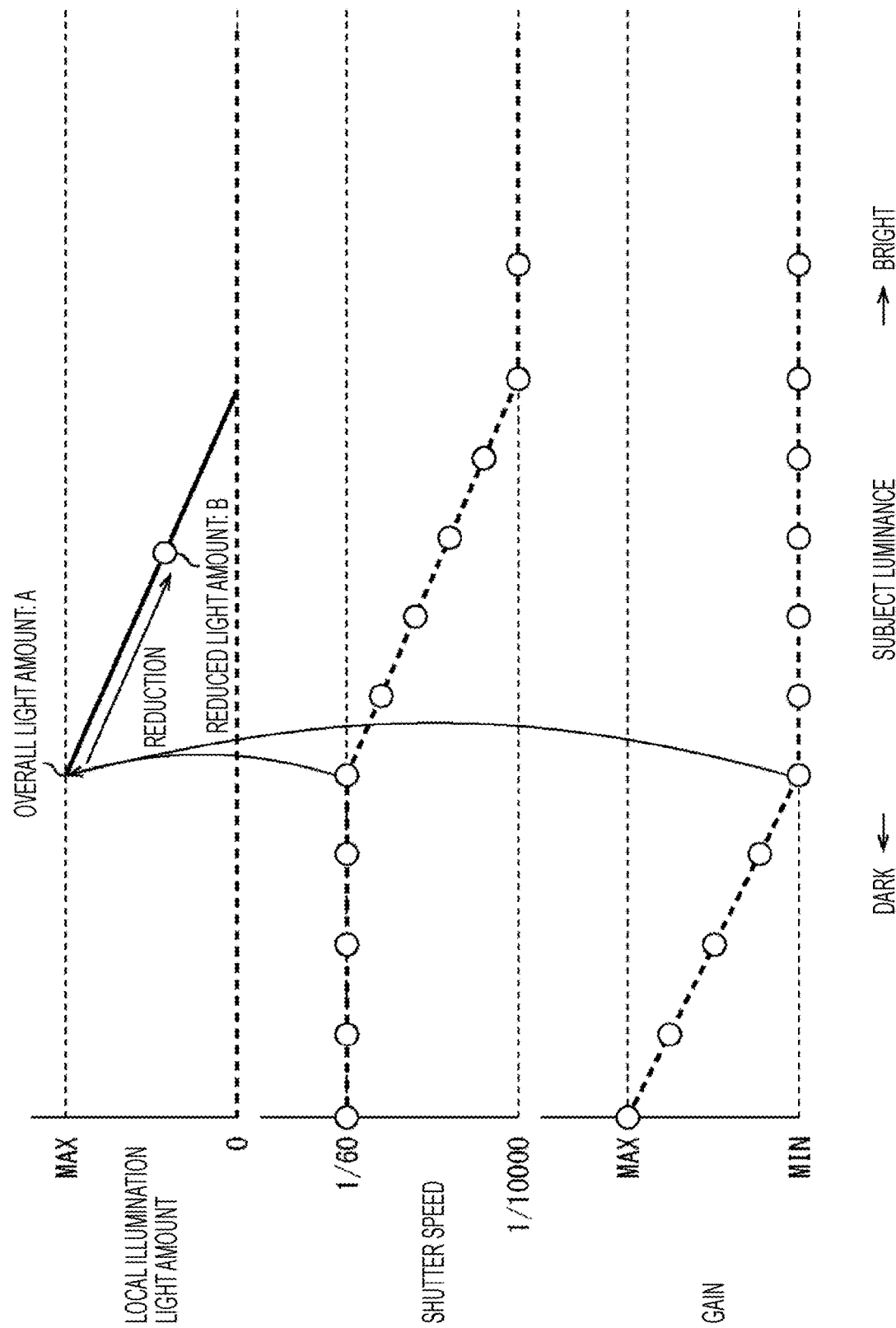
FIG. 7 is a diagram for describing an example of reducing a light amount of local illumination light.

FIG. 6 illustrates a program diagram used in local illumination light control processing.

In a program diagram illustrated in FIG. 6, a gain and shutter speed are the same as the gain and shutter speed in the program diagram in FIG. 5. Then, for each overall light amount obtained on the basis of individual gain and shutter speed, the local illumination light amount has a form of being reduced from each of the overall light amount according to luminance of a subject in the local region increasing.

An example of reducing a light amount of local illumination light when a gain is at a minimum value and shutter speed is 1/60 will be described with reference to FIG. 7.

First, the gain/shutter speed determination unit 32 puts emphasis on an SN ratio and shutter speed, and determines a gain and shutter speed of an overall screen, which cannot be changed for each local region. Then, the local illumination light amount determination unit 33 determines an overall light amount A from the gain and the shutter speed, and determines a local illumination light amount so as to reduce the local illumination light amount from the overall light amount for each local region according to luminance of a subject.

For example, in a case where a local region is not a high-luminance region, the local illumination light amount determination unit 33 determines the overall light amount A to be a light amount of illumination light in the local region. Meanwhile, in a case where a local region is a high-luminance region, the local illumination light amount determination unit 33 reduces from the overall light amount A according to a program diagram of the local illumination light amount, and determines a reduction light amount B that falls into a predetermined luminance range to be a local illumination light amount.

Then, the light amount coefficient calculation unit 34 calculates a reciprocal of a ratio of the reduction light amount B to the overall light amount A as a luminance coefficient (=overall light amount A/reduction light amount B).

<Local Illumination Light Control Processing>

Figure 8:
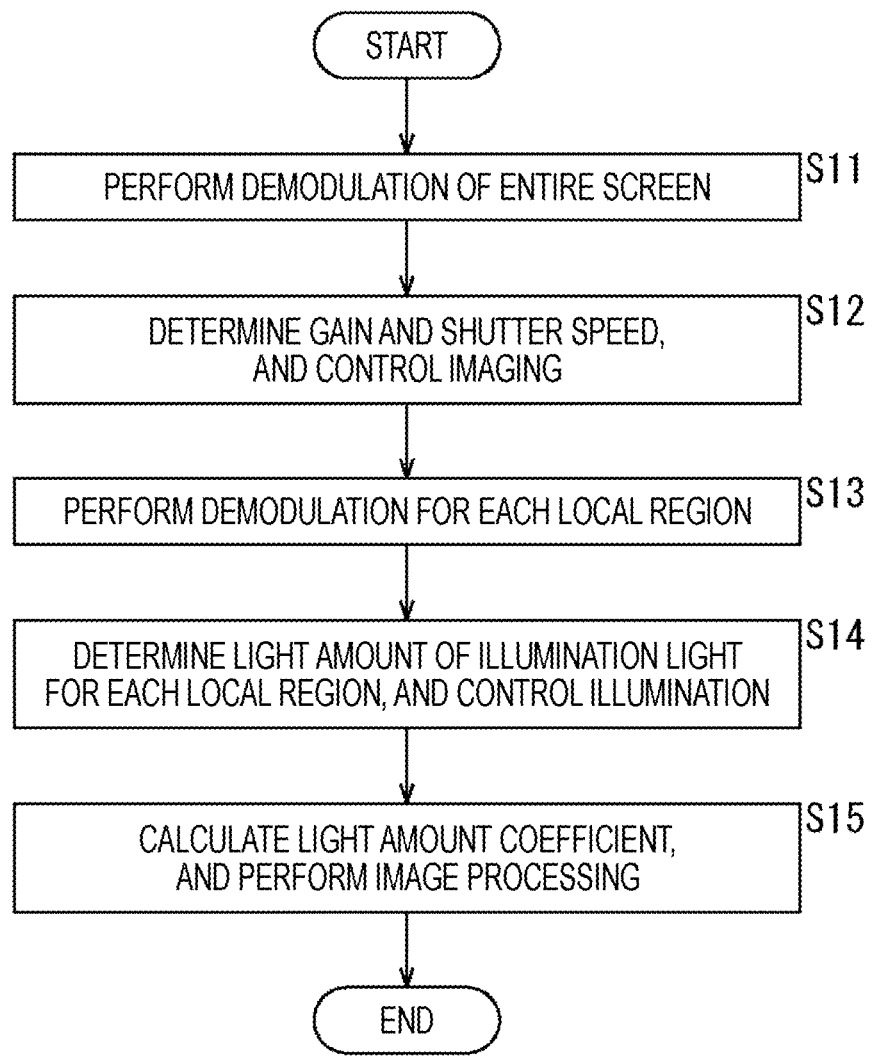
FIG. 8 is a flowchart for describing local illumination light control processing.

Local illumination light control processing performed in the local illumination control unit 24 will be described with reference to a flowchart in FIG. 8.

For example, when an image of an operative field is captured by the imaging device 12 is provided to the local illumination control unit 24, the processing starts. In Step S11, the demodulation processing unit 31 performs demodulation of the overall screen of the image provided from the imaging device 12, and provides the gain/shutter speed determination unit 32 with luminance information, which is obtained as a result.

In Step S12, the gain/shutter speed determination unit 32 determines a gain and shutter speed according to the luminance information of the overall screen, which is provided from the demodulation processing unit 31 in Step S11. Then, the gain/shutter speed determination unit 32 notifies the local illumination light amount determination unit 33 of the gain and the shutter speed, while instructing the imaging control unit 21 to perform control so that imaging is performed at the gain and the shutter speed.

In Step S13, the demodulation processing unit 31 performs demodulation on the image, which is provided from the imaging device 12, for each local region, and provides the local illumination light amount determination unit 33 with luminance information for each local region, which is obtained as a result.

In Step S14, the local illumination light amount determination unit 33 determines an overall light amount and a local illumination light amount as described above with reference to FIGS. 6 and 7. Then, the local illumination light amount determination unit 33 notifies the light amount coefficient calculation unit 34 of the overall light amount and the local illumination light amount, while instructing the local illumination control unit 24 to perform control so that irradiation with illumination light is performed according to the overall light amount and the local illumination light amount.

In Step S15, the light amount coefficient calculation unit 34 calculates a light amount coefficient on the basis of the overall light amount and the local illumination light amount notified in Step S14, and notifies the image processing unit 23 of the light amount coefficient. Image processing is performed in the image processing unit 23 by using the light amount coefficient, a local illumination HDR image acquired as a result of the image processing is displayed in the display device 15, and then the processing ends.

As described above, by performing local illumination light control processing for each one frame, the local illumination control unit 24 can always display a local illumination HDR image in which an operative field is better visible. That is, the local illumination control unit 24 can appropriately control a light amount of illumination light for each local region so that a high-luminance region is not generated for each one frame. For example, in a case where it is judged that a luminance value does not fall into a predetermined range by reduction of a light amount in a current frame, the local illumination control unit 24 can perform a high-speed feedback loop in which a light amount is further reduced in a subsequent frame in a repeated manner.

As a result, in the camera system for operation 11, it is possible to avoid generation of a high-luminance region at a high speed to an extent that the generation of the high-luminance region is unnoticeable just by looking at the display device 15. For example, although direct reflection by a scalpel increases sharply when a surgeon inserts the scalpel, the camera system for operation 11 can detect such a sharp change and reduce a light amount of the local region in which the scalpel is imaged.

Note that the local illumination control unit 24 may perform local illumination light control processing only when a sharp change in luminance (brightening/darkening) is detected, as well as may always perform the local illumination light control processing.

<Synchronous Local Illumination>

Synchronous local illumination performed in the camera system for operation 11 will be described with reference to FIG. 9.

For example, in a configuration in which the imaging device 12 adopts a CMOS image sensor, pixels are driven for each line by a so-called rolling shutter method.

Figure 9:
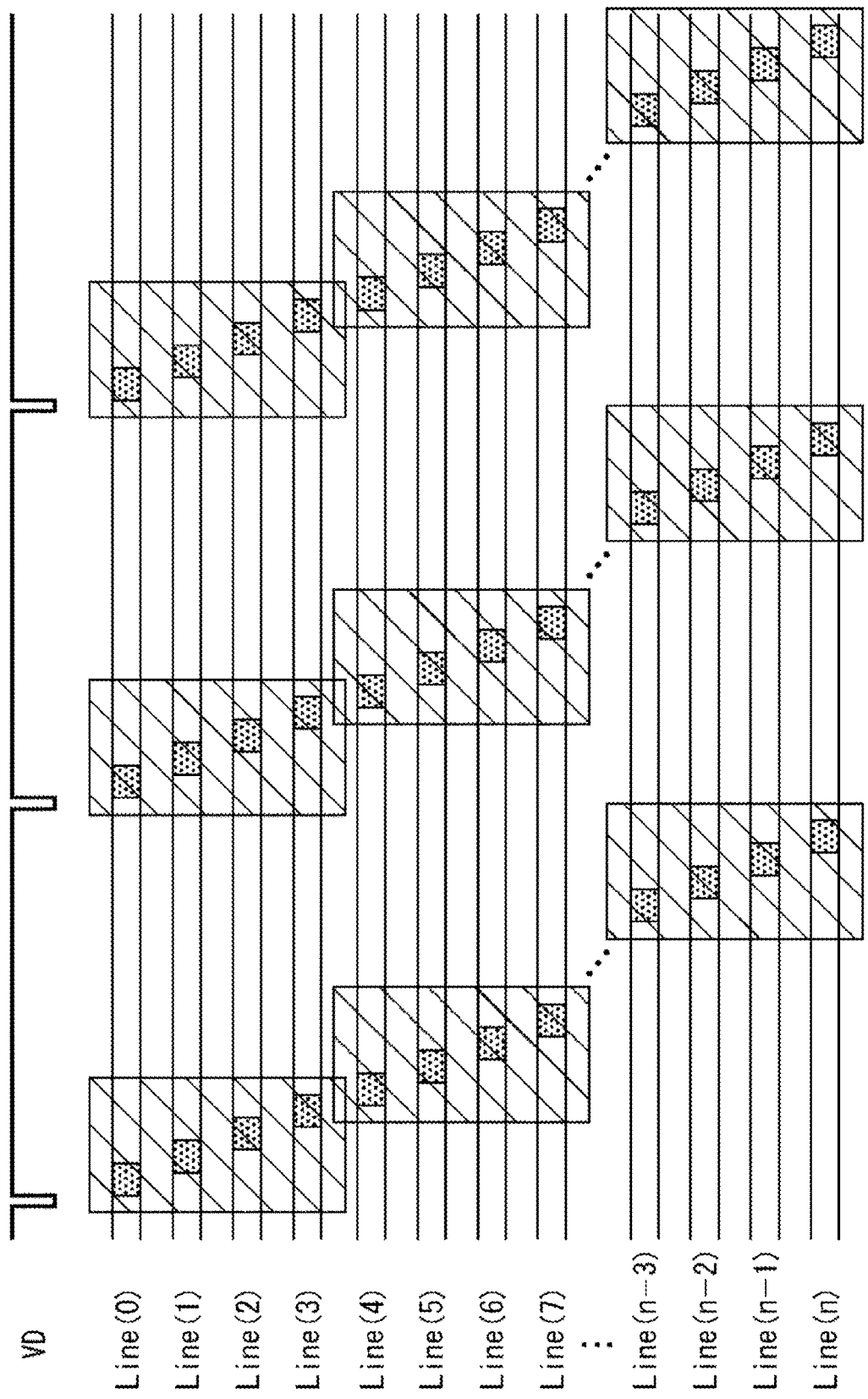
FIG. 9 is a diagram for describing synchronous local illumination.

That is, in an example illustrated in FIG. 9, regions with dot hatching represent accumulation time in which pixels for each line accumulate electric charge. Then, for each one frame of high-speed shutter according to a vertical drive signal VD, pixels of each line are sequentially driven from a line Line (0) toward a line Line (n) so as to accumulate electric charge.

Furthermore, in FIG. 9, regions with diagonal line hatching represent irradiation time during which irradiation with illumination light is performed for each local region in the illumination device 13 in accordance with a timing of high-speed shutter. As described above, the illumination device 13 can perform irradiation with the illumination light for each local region. Therefore, the illumination device 13 performs, for each predetermined number of lines, synchronous local illumination that controls a light emission timing so as to perform irradiation with illumination light in synchronization so as to include accumulation time for the lines with respect to a local region imaged with pixels of the lines.

In the example illustrated in FIG. 9, irradiation time is controlled for four lines each so as to include accumulation time for the four lines. That is, when imaging of one frame of an image starts, irradiation time is controlled so that accumulation time from a line Line (0) to a line Line (3) is included, and that a local region imaged with pixels from the line Line (0) to the line Line (3) is irradiated with illumination light. Next, irradiation time is controlled so that accumulation time from a line Line (4) to a line Line (7) is included, and that a local region of which image is captured with pixels from the line Line (4) to the line Line (7) is irradiated with illumination light. Similarity, when irradiation time is controlled, and imaging of one frame of an image ends, irradiation time is controlled so that accumulation time from a line Line (n−3) to a line Line (n) is included, and that a local region imaged with pixels from the line Line (n−3) to the line Line (n) is irradiated with illumination light.

Thus, an image with correct exposure over an overall screen can be acquired by the illumination device 13 performing synchronous local illumination so as to achieve a light emission timing synchronous with a shift of accumulation time in the rolling shutter method.

For example, in a case where overall strobe light emission is performed without performing synchronous local illumination, correct exposure cannot be achieved and a dim image without irradiation with illumination light is acquired in a line with accumulation time out of the light emission time. Meanwhile, irradiation with illumination light is performed during accumulation time for all lines by performing synchronous local illumination, and therefore an image can be acquired with correct exposure over an overall screen.

Moreover, by the illumination device 13 performing synchronous local illumination, time during which irradiation with illumination light is not performed is generated in a local region imaged with pixels of a line of one frame, the line not being applicable to exposure time. With this arrangement, for example, as compared to light emission that performs irradiation with illumination light during exposure time for all the lines, damage to a medically important subject (living body) can be alleviated by the illumination light.

Furthermore, as illustrated in FIG. 9, in a case where the illumination device 13 performs synchronous local illumination, irradiation with illumination light is controlled so that timings of performing irradiation with illumination light overlap with each other between adjacent irradiation times, and that irradiation regions irradiated with the illumination light overlap with each other. That is, irradiation times of illumination light (hatched regions in FIG. 9) are controlled so as to overlap each other in a line direction and in a time direction.

As described above, the camera system for operation 11 can acquire, by performing local illumination light control processing, a local illumination HDR image in which an operative field is better visible even with a configuration that uses the imaging device 12 including a small image sensor that captures an image with a normal dynamic range.

Furthermore, for example, with an imaging device that generates an HDR image by synthesizing a short-exposure image and a long-exposure image, temporal resolution is decreased by exposure times for acquiring the short-exposure image and the long-exposure image shift from each other. Alternatively, the spatial resolution is decreased because the positions of the pixels for acquiring the short-exposure image and the long-exposure image are deviated from each other.

Meanwhile, the camera system for operation 11 can acquire a better local illumination HDR image by avoiding a decrease in temporal resolution or spatial resolution.

Furthermore, although an image with uniform brightness can be acquired by an imaging device that synthesizes, by sequentially changing (moving) an irradiation position of illumination to change illumination intensity for example, a plurality of images in which a plurality of subjects is imaged with different illumination conditions, a delay occurs until the image is displayed.

Meanwhile, because the camera system for operation 11 does not require time for processing such as capturing and synthesizing a plurality of images, a delay until the images are displayed can be reduced, and the camera system for operation 11 can be used more preferably for an operation in which real-time image feedback is important, or the like.

Note that, in the camera system for operation 11, the illumination device 13 can be configured to change a wavelength of illumination light for each local region. For example, an operative field such as an organ tends to reflect a component of a specific wavelength range (for example, red). Thus, in a case where the demodulation processing unit 31 demodulates the component of a specific wavelength range exceeding a predetermined luminance range, the illumination device 13 can change a wavelength range of illumination light so as to reduce the component of the specific wavelength range (for example, can perform irradiation with green or blue light). With this arrangement, it is possible to reduce reflected light of the component of the specific wavelength range, while limiting reduction in brightness, and the camera system for operation 11 can acquire an image in which an operative field is better visible, according to the operative field.

Furthermore, in the camera system for operation 11, according to an area, location, distance, or the like of a high-luminance region in which saturation occurs, for example, a light amount of illumination light may be adjusted for each local region, as well as irradiation with illumination light may be turned off. For example, it is possible to acquire an image in which an operative field is better visible by performing local illumination light control processing that turns off irradiation with illumination light with respect to a local region corresponding to an affected area close to the imaging device 12 and the illumination device 13.

Specifically, in a case where the camera system for operation 11 is utilized in otorhinolaryngology for observing an ear hole with an endoscope, saturation is likely to occur in a region where a wall around the ear hole is imaged, and therefore overall visual recognition is expected to be difficult. Therefore, in the camera system for operation 11, it is possible to set an otorhinolaryngology mode and perform local illumination light control processing to turn off the irradiation with illumination light with respect to a local region corresponding to a wall around an ear hole.

Similarly, for example, in a case where the camera system for operation 11 is utilized in neurosurgery, it is possible to set a neurosurgery mode and perform local illumination light control processing to brighten a local region deep inside a brain and darken (turn off irradiation with illumination light) other local regions. Furthermore, in a case where the camera system for operation 11 is utilized in ophthalmology, it is possible to set an ophthalmology mode and perform local illumination light control processing to darken irradiation with illumination light with respect to a local region corresponding to an optic papilla.

Moreover, the camera system for operation 11 may include, for example, a line-of-sight detection unit that detects a line of sight of a surgeon, and local illumination light control processing may be performed only when it is detected that the surgeon is looking at the display device 15.

With this arrangement, local illumination light control processing is stopped when the surgeon is not looking at the display device 15, for example, when the surgeon is visually recognizing an affected area directly. That is, although it is bothersome that a light amount of illumination light changes frequently when the surgeon is visually recognizing the affected area directly, such bothersomeness can be avoided. Note that a switch that instructs whether or not the camera system for operation 11 performs local illumination light control processing may be provided, and operation of the switch may stop the local illumination light control processing when the surgeon is visually recognizing an affected area directly.

Note that, in addition to adopting a projector as described above as the illumination device 13, for example, a method for adjusting brightness with respect to a center or outer circumference of an illumination region with a mirror control method, a method for partially turning off a point light source with illumination including a plurality of point light sources, or the like may be adopted. Furthermore, as the illumination device 13, a method for adjusting brightness with blinking of laser light may be adopted by using scan type illumination utilizing illumination for which laser light is scanned by a micro electro mechanical systems (MEMS) mirror, a polygon mirror, or the like.

Furthermore, it is possible to reduce a light amount of illumination light in a desired local region by mounting a movable neutral density (ND) filter on the illumination device 13, and moving the ND filter to a part desired to be darkened. Furthermore, a light amount of illumination light in a desired local region may be reduced by utilizing a digital micromirror device (DMD) element. Thus, various kinds of other illumination control methods can be adopted for the illumination device 13.

Furthermore, a configuration in which a side of the controller 14 includes an illumination control optical system is preferred for miniaturization of an autoclave or the illumination device 13. For example, in a configuration in which light is transmitted from the controller 14 to the illumination device 13 via an optical fiber, the optical fiber eliminates anisotropy, and therefore only a center or outer circumference of illumination can be darkened. Therefore, it is possible to darken any position by moving the center of illumination.

By the way, in general, if reflected light due to specular reflection is completely suppressed, appearance is such that a glossy feeling of water, oil, or the like disappears. Furthermore, reflected light of only one point may not be felt bothersome. Therefore, the camera system for operation 11 may be configured such that a glossy feeling of water, oil, or the like is avoided from disappearing by limiting a degree of reducing a light amount of illumination light for reflected light of only one point.

Furthermore, in the camera system for operation 11, local illumination light control processing may be controlled to be stopped depending on a type of image processing performed on an image by the image processing unit 23. For example, when the image processing unit 23 performs high resolution processing (for example, image correction processing such as super-resolution), it is better to stop local illumination light control processing to acquire a good image.

<Configuration Example of Computer>

Next, a series of processing (control method) described above can be performed by hardware or software. In a case where a series of processing is performed by software, a program constituting the software is installed on a general-purpose computer, or the like.

Figure 10:
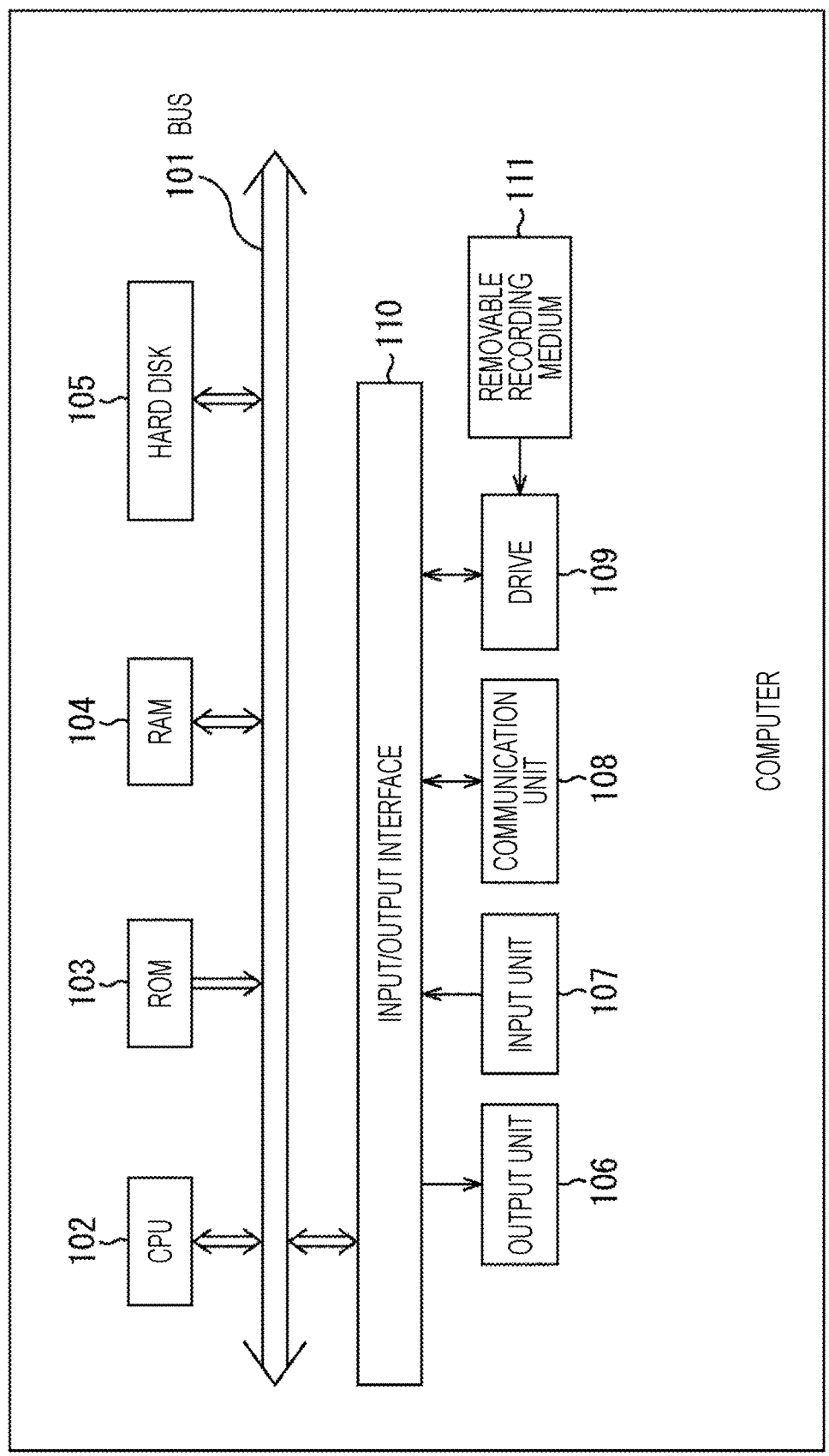
FIG. 10 is a block diagram illustrating a configuration example of an embodiment of a computer to which the present technology is applied.

FIG. 10 is a block diagram illustrating a configuration example of an embodiment of a computer on which a program for executing the above-described series of processing is installed.

It is possible to previously record a program in a hard disk 105 or ROM 103 as a recording medium, which is incorporated in a computer.

Alternatively, the program can be stored (recorded) in a removable recording medium 111 driven by a drive 109. Such a removable recording medium 111 can be provided as so-called packaged software. Here, examples of the removable recording medium 111 include a flexible disk, a compact disc read only memory (CD-ROM), a magneto optical (MO) disk, a digital versatile disc (DVD), a magnetic disk, and a semiconductor memory, for example.

Note that a program can be installed on a computer from the removable recording medium 111 as described above, as well as can be downloaded to the computer via a communication network or a broadcasting network and installed on the hard disk 105 incorporated. That is, for example, the program can be wirelessly transferred from a download site to the computer via an artificial satellite for digital satellite broadcasting, or transferred to the computer by wire via a network such as a local area network (LAN) or the Internet.

The computer has a built-in central processing unit (CPU) 102, and an input/output interface 110 is connected to the CPU 102 via a bus 101.

When a command is input by a user operating an input unit 107, or the like, via the input/output interface 110, the CPU 102 executes a program stored on the read only memory (ROM) 103 accordingly. Alternatively, the CPU 102 loads a program stored on the hard disk 105 into a random access memory (RAM) 104 and executes the program.

With this arrangement, the CPU 102 performs processing according to the above-described flowchart or processing performed according to the above configuration described with the block diagram. Then, as necessary, the CPU 102 outputs a processing result from an output unit 106, transmits the processing result from a communication unit 108, causes the hard disk 105 to record the processing result, or the like, via the input/output interface 110, for example.

Note that the input unit 107 includes a keyboard, a mouse, a microphone, or the like. Furthermore, the output unit 106 includes a liquid crystal display (LCD), a speaker, or the like.

Here, in the present specification, processing performed by a computer according to the program does not necessarily have to be performed in time series in an order described as a flowchart. That is, processing performed by the computer according to a program also includes processing that is executed in parallel or individually (for example, parallel processing or object processing).

Furthermore, the program may be processed by one computer (processor) or may be subjected to distributed processing by a plurality of computers. Moreover, the program may be transferred to a distant computer and executed.

Moreover, in the present specification, the system means a set of a plurality of components (devices, modules (parts), or the like) without regard to whether or not all the components are in the same housing. Therefore, a plurality of devices housed in separate housings and connected via a network, and one device housing a plurality of modules in one housing are both systems.

Furthermore, for example, a configuration described as one device (or processing unit) may be divided and configured as a plurality of devices (or processing units). To the contrary, the configurations described above as a plurality of devices (or processing units) may be collectively configured as one device (or processing unit). Furthermore, needless to say, a configuration other than the configurations described above may be added to a configuration of each device (or each processing unit). Moreover, if a configuration and operation of an entire system are substantially the same, a part of a configuration of a certain device (or processing unit) may be included in a configuration of another device (or another processing unit).

Furthermore, for example, the present technology can have one configuration of cloud computing in which one function is shared and processed jointly by a plurality of devices via a network.

Furthermore, for example, the above-described programs can be executed in any device. In that case, the device is only required to have a necessary function (function block, or the like) so that necessary information can be acquired.

Furthermore, for example, each step described in the above-described flowchart can be executed by one device, or can be executed by being shared by a plurality of devices. Moreover, in a case where a plurality of pieces of processing is included in one step, the plurality of pieces of processing included in the one step can be executed by being shared by a plurality of devices, in addition to being executed by one device. In other words, a plurality of pieces of processing included in one step can be executed as a plurality of steps. To the contrary, pieces of processing described as a plurality of steps can be collectively executed as one step.

Note that, the program executed by the computer may be a program in which processing of steps describing the program is executed in time series in an order described in the present specification, or a program in which the processing may be executed in parallel, or individually at a necessary timing such as when a call is made. That is, unless there is a contradiction, the processing of each step may be executed in an order different from the order described above. Moreover, the processing of steps describing the program may be executed in parallel with processing of another program, or may be executed in combination with processing of another program.

Note that the plurality of present technologies described in the present specification can be implemented independently as a single piece unless there is a contradiction. Needless to say, any of the plurality of present techniques can be used in combination. For example, a part or all of the present technology described in any of the embodiments can be implemented in combination with a part or all of the present technology described in another embodiment. Furthermore, a part or all of the present technology described above can be implemented in combination with another technology not described above.

<Example of Configuration Combination>

Note that the present technology can have the following configurations.

(1)

An imaging system including:

an imaging device that images a predetermined imaging area;

an illumination device that performs irradiation with illumination light so as to illuminate the imaging area and is capable of adjusting a light amount of the illumination light for each of local regions narrower than the imaging area; and a control unit that controls the imaging device and the illumination device, in which the control unit has a detection unit that detects a high-luminance region having a luminance value exceeding a predetermined luminance range in an image captured by the imaging device, and has a light amount determination unit that determines a light amount of the illumination light with which the illumination device irradiates the local region corresponding to the high-luminance region to be a reduction light amount reduced to be less than a light amount with respect to overall of the imaging area.

(2)

The imaging system according to (1) described above, the imaging system further including an image processing unit that performs image processing to amplify a luminance value of the image corresponding to the local region irradiated with the illumination light with the reduction light amount, according to a ratio of the reduction light amount to an overall light amount that is a light amount with respect to the overall of the imaging area.

(3)

The imaging system according to (2) described above, the imaging system further including:

a determination unit that determines a gain and shutter speed for when the imaging device captures an image on the basis of luminance information that indicates brightness of an overall screen of the image, in which the light amount determination unit determines the overall light amount according to the gain and shutter speed determined by the determination unit, and determines the reduction light amount so that, with respect to the local region to be the high-luminance region when irradiation is performed with the illumination light with the overall light amount, a luminance value in the local region falls within the luminance range.

(4)

The imaging system according to (3) described above, the imaging system further including a calculation unit that calculates a light amount coefficient that the image processing unit uses for image processing on the basis of the overall light amount and reduction light amount determined by the light amount determination unit.

(5)

The imaging system according to any one of (1) to (4) described above, in which the illumination device performs irradiation with the illumination light in synchronization with exposure time for each of pixels of the imaging device.

(6)

The imaging system according to (5) described above, in which the imaging device captures the image with a rolling shutter method by which exposure of the pixels is sequentially performed for each line, and the illumination device sequentially performs irradiation with the illumination light for each local region during irradiation time including the exposure time in a line of the pixels corresponding to each of the local regions.

(7)

The imaging system according to (6) described above, in which the illumination device controls irradiation with the illumination light so that irradiation time for each of the local regions overlaps between the local regions adjacent to each other in a direction orthogonal to the line of the pixels at a predetermined interval.

(8)

The imaging system according to according to any one of (1) to (7) described above, in which the illumination device is able to change a wavelength range of the illumination light, and, in a case where a component of a specific wavelength range exceeds a predetermined luminance range in the local region, changes a wavelength range of the illumination light with which the local region is irradiated to reduce the specific wavelength range.

(9)

A control device that controls an imaging device that images a predetermined imaging area and an illumination device that performs irradiation with illumination light so as to illuminate the imaging area and is capable of adjusting a light amount of the illumination light for each of local regions narrower than the imaging area, the control device including:

a detection unit that detects a high-luminance region having a luminance value exceeding a predetermined luminance range in an image captured by the imaging device; and a light amount determination unit that determines a light amount of the illumination light with which the illumination device irradiates the local region corresponding to the high-luminance region to be a reduction light amount reduced to be less than a light amount with respect to overall of the imaging area.

(10)

A control method including, by a control device that controls an imaging device that images a predetermined imaging area and an illumination device that performs irradiation with illumination light so as to illuminate the imaging area and is capable of adjusting a light amount of the illumination light for each of local regions narrower than the imaging area:

detecting a high-luminance region having a luminance value exceeding a predetermined luminance range in an image captured by the imaging device; and determining a light amount of the illumination light with which the illumination device irradiates the local region corresponding to the high-luminance region to be a reduction light amount reduced to be less than a light amount with respect to overall of the imaging area.

Note that, the present embodiment is not limited to the above-described embodiment, and various changes can be made without departing from the scope of the present disclosure. Furthermore, the effects described herein are only examples, and the effects of the present technology are not limited to these effects. Additional effects may also be obtained.

REFERENCE SIGNS LIST

11 Camera system for operation
12 Imaging device
13 Illumination device
14 Controller
15 Display device
21 Imaging control unit
22 Light source control unit
23 Image processing unit
24 Local illumination control unit
31 Demodulation processing unit
32 Gain/shutter speed determination unit
33 Local illumination light amount determination unit
34 Light amount coefficient calculation unit

The invention claimed is:

1. An imaging system, comprising:
an imaging device that images a predetermined imaging area;
an illumination device that performs irradiation with illumination light so as to illuminate the imaging area and is capable of adjusting a light amount of the illumination light for each of local regions narrower than the imaging area; and
processing circuitry configured to control the imaging device and the illumination device, wherein
the processing circuitry is configured to
detect a high-luminance region having a luminance value exceeding a predetermined luminance range in an image captured by the imaging device,
determine a light amount of the illumination light with which the illumination device irradiates the local region corresponding to the high-luminance region to be a reduction light amount reduced to be less than a light amount with respect to overall of the imaging area, and
perform image processing to amplify a luminance value of the image corresponding to the local region irradiated with the illumination light with the reduction light amount, according to a ratio of the reduction light amount to an overall light amount that is a light amount with respect to the overall of the imaging area.

2. The imaging system according to claim 1, wherein the processing circuitry is configured to:
determine a gain and shutter speed for when the imaging device captures an image on a basis of luminance information that indicates brightness of an overall screen of the image,
determine the overall light amount according to the gain and shutter speed determined by the determination unit, and
determine the reduction light amount so that, with respect to the local region to be the high-luminance region when irradiation is performed with the illumination light with the overall light amount, a luminance value in the local region falls within the luminance range.

3. The imaging system according to claim 2, wherein the processing circuitry is configured to calculate a light amount coefficient used for image processing on a basis of the overall light amount and the reduction light amount.

4. The imaging system according to claim 1, wherein the illumination device performs irradiation with the illumination light in synchronization with exposure time for each of pixels of the imaging device.

5. The imaging system according to claim 4, wherein the imaging device captures the image with a rolling shutter method by which exposure of the pixels is sequentially performed for each line, and
the illumination device sequentially performs irradiation with the illumination light for each local region during irradiation time including the exposure time in a line of the pixels corresponding to each of the local regions.

6. The imaging system according to claim 5, wherein the illumination device controls irradiation with the illumination light so that irradiation time for each of the local regions overlaps between the local regions adjacent to each other in a direction orthogonal to the line of the pixels at a predetermined interval.

7. The imaging system according to claim 1, wherein the illumination device is configured to:
   change a wavelength range of the illumination light, and
   in a case where a component of a specific wavelength range exceeds a predetermined luminance range in the local region, change a wavelength range of the illumination light with which the local region is irradiated to reduce the specific wavelength range.

8. A control device, comprising:
   processing circuitry configured to
   control an imaging device that images a predetermined imaging area and an illumination device that performs irradiation with illumination light so as to illuminate the imaging area and is capable of adjusting a light amount of the illumination light for each of local regions narrower than the imaging area;
   detect a high-luminance region having a luminance value exceeding a predetermined luminance range in an image captured by the imaging device;
   determine a light amount of the illumination light with which the illumination device irradiates the local region corresponding to the high-luminance region to be a reduction light amount reduced to be less than a light amount with respect to overall of the imaging area; and
   perform image processing to amplify a luminance value of the image corresponding to the local region irradiated with the illumination light with the reduction light amount, according to a ratio of the reduction light amount to an overall light amount that is a light amount with respect to the overall of the imaging area.

9. The control device according to claim 8, wherein the processing circuitry is configured to:
   determine a gain and shutter speed for when the imaging device captures an image on a basis of luminance information that indicates brightness of an overall screen of the image,
   determine the overall light amount according to the gain and shutter speed determined by the determination unit, and
   determine the reduction light amount so that, with respect to the local region to be the high-luminance region when irradiation is performed with the illumination light with the overall light amount, a luminance value in the local region falls within the luminance range.

10. The control device according to claim 9, wherein the processing circuitry is configured to calculate a light amount coefficient used for image processing on a basis of the overall light amount and the reduction light amount.

11. An imaging system, comprising:
   an imaging device that images a predetermined imaging area;
   an illumination device that performs irradiation with illumination light so as to illuminate the imaging area and is capable of adjusting a light amount of the illumination light for each of local regions narrower than the imaging area; and
   processing circuitry configured to control the imaging device and the illumination device, wherein
   the processing circuitry is configured to
      detect a high-luminance region having a luminance value exceeding a predetermined luminance range in an image captured by the imaging device, and
      determine a light amount of the illumination light with which the illumination device irradiates the local region corresponding to the high-luminance region to be a reduction light amount reduced to be less than a light amount with respect to overall of the imaging area,
   the illumination device performs irradiation with the illumination light in synchronization with exposure time for each of pixels of the imaging device,
   the imaging device captures the image with a rolling shutter method by which exposure of the pixels is sequentially performed for each line,
   the illumination device sequentially performs irradiation with the illumination light for each local region during irradiation time including the exposure time in a line of the pixels corresponding to each of the local regions, and
   the illumination device controls irradiation with the illumination light so that irradiation time for each of the local regions overlaps between the local regions adjacent to each other in a direction orthogonal to the line of the pixels at a predetermined interval.

* * * * *